(12) United States Patent
Shaw et al.

(10) Patent No.: US 12,144,522 B2
(45) Date of Patent: Nov. 19, 2024

(54) DEVICES FOR TISSUE TREATMENT AND METHODS OF USE THEREOF

(71) Applicant: TendoNova Corporation, Atlanta, GA (US)

(72) Inventors: Jonathan Shaw, Atlanta, GA (US);
Brett Rogers, Atlanta, GA (US);
Shawna Hagen, Atlanta, GA (US);
Luka Grujic, Boston, MA (US);
Kenneth R. Mautner, Atlanta, GA (US)

(73) Assignee: TendoNova Corporation, Atlanta, GA (US)

( * ) Notice: Subject to any disclaimer, the term of this patent is extended or adjusted under 35 U.S.C. 154(b) by 1023 days.

(21) Appl. No.: 17/045,298

(22) PCT Filed: Apr. 2, 2019

(86) PCT No.: PCT/US2019/025297
§ 371 (c)(1),
(2) Date: Oct. 5, 2020

(87) PCT Pub. No.: WO2019/195221
PCT Pub. Date: Oct. 10, 2019

(65) Prior Publication Data
US 2021/0145477 A1 May 20, 2021

Related U.S. Application Data

(60) Provisional application No. 62/653,712, filed on Apr. 6, 2018.

(51) Int. Cl.
*A61B 17/34* (2006.01)
*A61B 90/00* (2016.01)
*A61B 17/00* (2006.01)

(52) U.S. Cl.
CPC ...... *A61B 17/3476* (2013.01); *A61B 17/3403* (2013.01); *A61B 90/06* (2016.02);
(Continued)

(58) Field of Classification Search
CPC ............ A61B 17/3476; A61B 17/3403; A61B 2017/00075; A61B 2017/00876;
(Continued)

(56) References Cited

U.S. PATENT DOCUMENTS 5,432,459 A 7/1995 Thompson et al.
9,987,468 B2 * 6/2018 Bagwell ........... A61B 5/150389
(Continued)

FOREIGN PATENT DOCUMENTS

JP 2014-513564 A 6/2014

OTHER PUBLICATIONS

Extended European Search Report issued in European Application No. 19780831.4, date of mailing: Dec. 17, 2021, 8 pages.
(Continued)

*Primary Examiner* — Julian W Woo
(74) *Attorney, Agent, or Firm* — Brown Rudnick LLP; Adam M. Schoen

(57) ABSTRACT

The invention provides systems and methods for monitoring a status of targeted tissue undergoing a procedure via a medical device, such as, for example, a tenotomy, and further providing feedback associated with one or more parameters of the targeted tissue in real-time to thereby indicate a completeness of the procedure to an operator of the medical device. The invention also provides devices with a magnetic coupling of components and methods of use of such devices.

8 Claims, 12 Drawing Sheets

(52) U.S. Cl.
CPC ............... *A61B 2017/00026* (2013.01); *A61B 2017/00075* (2013.01); *A61B 2017/00876* (2013.01); *A61B 2017/3413* (2013.01); *A61B 2090/064* (2016.02)

(58) Field of Classification Search
CPC .......... A61B 17/3478; A61B 17/32002; A61B 2017/00022; A61B 2017/320028
See application file for complete search history.

(56) References Cited

U.S. PATENT DOCUMENTS

| | | |
|---|---|---|
| 9,993,259 B2 * | 6/2018 | Barnes ........... A61B 17/320036 |
| 2011/0160620 A1 | 6/2011 | Gill et al. |
| 2011/0196404 A1 | 8/2011 | Dietz et al. |
| 2012/0209303 A1 * | 8/2012 | Frankhouser ...... A61B 17/3476 |
| | | 606/169 |
| 2015/0283334 A1 | 10/2015 | Marx et al. |
| 2015/0366569 A1 | 12/2015 | Miller |
| 2016/0059043 A1 | 3/2016 | Gill et al. |
| 2017/0007271 A1 | 1/2017 | Miller et al. |
| 2017/0049468 A1 | 2/2017 | Mautner et al. |

OTHER PUBLICATIONS

International Search Report and Written Opinion issued in International Application No. PCT/US2019/025297, date of mailing: Jul. 30, 2019, 9 pages.

\* cited by examiner

DEVICES FOR TISSUE TREATMENT AND METHODS OF USE THEREOF

CROSS-REFERENCE TO RELATED APPLICATION(S)

This application claims priority to, and the benefit of, U.S. Provisional Application No. 62/653,712, filed on Apr. 6, 2018, the content of which is incorporated by reference herein in its entirety.

FIELD OF THE INVENTION

The invention generally relates to improved devices for tissue treatment that include a feedback sensor and methods of use thereof. The invention also relates to additional improvements of such devices, such as an improved magnetic interface between device components.

BACKGROUND

Overuse of musculoskeletal tissues, such as tendons, plantar fascia, etc., can result in chronic degenerative tissue (e.g., tendinopathy, plantar fasciitis, etc.), thereby leading to pain and disability. For example, tendinopathy (disease of the tendon) or tendinosis is a non-inflammatory degeneration of the tendon, usually due to excessive repetitive strain and injury. The development of tendinopathies (or tendinosis) can be caused by repeated mechanical trauma or microtrauma caused by overuse and/or repetitive increased stress/demand on the tendon, which over time, leads to degeneration/breakdown of the normal tendon tissue. Whether mechanical, vascular, or some combination thereof, the final result is that a tendon becomes damaged, dysfunctional, and can no longer heal itself completely after repetitive trauma.

The damaged tissue is typically treated with NSAIDS, corticosteroid injections, physical therapy, platelet rich plasma injections, or surgery, including a tenotomy procedure. Percutaneous needle tenotomy (PNT), for example, is a minimally invasive procedure in which a needle is advanced through the skin, generally under the direct visual guidance of using ultrasound, and directed to a target tissue to make break up (i.e., puncture, piece, slice, etc.) the tissue (e.g., scarred tissue, degenerated tissue, pathological tissue, etc.). The intent of a PNT procedure is to cause microtrauma and breaks in the tissue, which, in turn, induces an acute injury and causes local inflammation, thereby increasing the circulation to the area, restarting the healing cycle and helping new, healthy tissue to form. This process will ultimately repair/heal the degenerated tendons.

While current PNT techniques do have some success in treating musculoskeletal tissue issues, such techniques have drawbacks. For example, a physician or other medical professional, typically performs a PNT with manual repeated fenestration of the tissue with a needle or similar apparatus, which can lead to inconsistency from procedure to procedure, and further result in incomplete repair due to lack of incomplete tissue disruption. More recently, devices have been developed to perform this procedure. However, even with the use of such devices, there is inconsistency in the procedure and variability in procedure results.

SUMMARY

The invention recognizes that effectiveness of a tissue debridement procedure is related to degree of tissue disruption. Particularly, the invention recognizes that there is a perceivable decrease in (or increase in uniformity of) puncture resistance as a level of tissue disruption increases. Accordingly, the invention realizes that measuring tissue resistance (e.g., tendon tissue resistance) during a mechanical tissue debridement procedure (e.g., tenotomy) provides an objective benchmark by which an operator can base a decision of successful completion of the procedure.

Accordingly, the present invention overcomes current tissue treatment techniques by providing improved tissue treatment devices that include a feedback element (e.g., sensor). Such a feedback element allows an operator to monitor the status of tissue at a targeted tissue site while a patient is undergoing a procedure, for example, a PNT procedure. An exemplary feedback element (e.g. sensor) allows for monitoring or measuring tissue resistance. In such an embodiment, the feedback sensor is configured to detect tissue resistance as the tissue is undergoing treatment (i.e., during debridement or puncturing of the tissue). The information or data from the sensor is transmitted to a processor (housed locally within the device or remotely on a separate device, such as a smart phone). The processor correlates the detected tissue resistance with a level of tissue disruption and, in turn, determines the level of completion of the procedure. That information is then displayed to an operator, either on the device itself or on a separate device. In that manner, the devices of the invention provide real-time feedback to an operator of the medical device during the procedure, wherein such feedback provides an indication of the level of completeness of the procedure. Accordingly, the present invention is able to provide an operator (i.e., surgeon, physician, or other medical professional) with an accurate indication of tissue disruption with each procedure, thereby ensuring that a targeted tissue site is adequately treated and the level of anticipated repair is optimal. Importantly, improved devices of the invention with a feedback sensor reduce variability in clinical outcomes from patient to patient and from physician to physician.

Certain aspects of the invention relate to a tissue treating device. In one embodiment, the device comprises a body including a first portion and a second portion, wherein the second portion includes a tissue penetrating element that extends from a distal end of the body and is oscillated by a motor housed within the body and operably associated with the tissue penetrating element. The device further comprises a feedback sensor operably associated with the device that transmits feedback to a processor that provides an operator as to a status of a tissue that has been penetrated one or more times by the tissue penetrating element. The feedback sensor transmits feedback to the processor in real-time, or near real-time and the processor provides an operator as to a status of the tissue in real-time, or near real-time. The feedback sensor is configured to directly or indirectly detect resistance of the tissue that has been penetrated by the tissue penetrating element. More specifically, the feedback sensor may be configured to sense a various parameters associated with components of the device during operation thereof and related to a resistance of the tissue, including, but not limited to, a pressure force associated with the tissue, an electrical current associated with operation of the motor, an output of the motor associated with a rotation speed of a drive shaft of the motor, and the like. Accordingly, the feedback sensor may include a piezoelectric sensor, a current sensor, and/or a tachometer or rotary encoder, for example.

The processor is configured to correlate the detected tissue resistance with a level of tissue disruption and further determine a level of completeness of a treatment of the tissue based, at least in part, on the correlation. The processor is configured to output the status of the tissue to a display, wherein the display is provided either locally on the tissue treating device itself or provided remotely on a separate device. It should be further noted that the processor is either provided locally within the housing of the tissue treating device itself or provided remotely on a separate device (i.e., a separate computer, tablet, laptop, smartphone, etc.). Accordingly, the feedback sensor and processor may be configured to wirelessly communicate and exchange data via any known wireless communication protocol, such as cellular-based data communication technologies, Bluetooth radio, Near Field Communication (NFC), internet or wireless networks, and other networks capable of carrying data. The status of the tissue provided by the processor may relate to one or more parameters associated with the tissue itself or the treatment, including, but not limited to, an actual number value and/or a scaled readout of tissue resistance, power required to overcome tissue resistance, force to overcome tissue resistance, and an indication of the level of completeness of the treatment (i.e., a percentage of total completion based on a 100 percent scale).

The first and second portions can form a single unitary body. Alternatively, the first and second portions and be first and second parts that are joined together to form the body. In certain embodiments, the first portion is a reusable portion and the second portion is a disposable portion. In such embodiments, the first portion includes the motor and the second portion includes the tissue penetrating element. The feedback sensor can be located in either the first or second portion and may preferably be located in the first portion.

Other aspects of the invention provide a tissue penetrating device with a magnetic interface for the components of the device. In one embodiment, the device comprises a first portion housing a motor and a second portion housing a tissue penetrating element, wherein the tissue penetrating element is operably coupled to the motor via a magnetic coupling, which coupling resides on a single side of a sterile field. Such devices provide an easy coupling for an operator between the reusable portion and the disposable portion, particularly when it is important to maintain a sterile surgical field. In such situations, the operator does not have to risk breaching the field to couple together the two components of the device. Rather, simply bringing the components proximate each other is enough to initiate the magnetic coupling to form a completely ready-to-use device.

For example, in certain embodiments, the magnetic coupling includes an attachment member housed within the second portion. The attachment member includes a housing including a closed proximal end and an open distal end and a length defined therebetween, wherein an edge of the open distal end is sealed into engagement with an interior of the second portion, thereby isolating an interior of the housing from a remainder of the first and second portions of the tissue penetrating device. By isolating the interior of the attachment member from the remainder of the second portion of the device, as well as the first portion of the device, a sterile field is effective created within the interior of the first and second portions, as the tissue penetrating element is effectively isolated from any interior of the first and second portions and limited to placement within the attachment member. The open distal end of the attachment member is generally aligned with an opening at a distal end of the second portion such that distal portion of the tissue penetrating element extends therethrough and into the interior of the housing of the attachment member, wherein the distal end of the tissue penetrating element engages and is releasably retained within the closed proximal end of the attachment member. The proximal end of the attachment member includes a magnetic coupling member coupled to a corresponding magnetic coupling member provided on a linear oscillating member operably coupled to the motor. Accordingly, the magnetic coupling interface resides on a single side of the sterile field (i.e., within the second portion of the device), as opposed to having to cross a sterile field in order to couple the tissue penetrating element and the second portion of the device to one another. Thus, when the linear oscillating member is oscillated by the motor, the linear oscillating member further oscillates the proximal end of the attachment member and thereby oscillates the tissue penetrating element. The housing of the attachment member comprises a flexible wall configured to expand and compress in a longitudinal direction along a length of the housing from a distal end to a proximal end to accommodate oscillation.

In some embodiments, the tissue penetrating device further includes a gear assembly operably coupled to the motor and the tissue penetrating element, wherein the gear assembly is configured to convert rotary motion of the motor to linear motion to oscillate the tissue penetrating element. The gear assembly may generally include a first bevel gear directly coupled to a drive shaft of the motor and having an axis aligned with an axis of the drive shaft to thereby correspondingly rotate with the drive shaft about a common axis and a second bevel gear positioned relative to the first bevel gear such that the second bevel gear axis is approximately orthogonal to the first bevel gear axis and tooth-bearing faces of the first and second bevel gears correspondingly engage one another. The tissue penetrating device may further include a connecting rod having a first end directly coupled to a portion of the second bevel gear and a second end directly coupled the linear oscillating member, wherein the connecting rod oscillates in response to rotation of the first bevel gear, thereby resulting in oscillation of the linear oscillating member.

Once a procedure is complete, an operator need only disengage the tissue penetrating element from the attachment member by simply pulling the tissue penetrating element out of engagement with the attachment member, wherein the used tissue penetrating element can either be discarded or set aside for sterilization, and a new or sterile tissue penetrating element can be coupled to the attachment member. Thus, the tissue penetrating device allows for a relatively simple process of changing out tissue penetrating elements without the risk of breaching a sterile field of the device, thereby allowing for the device to be reused for multiple procedures with little to no risk of contamination. The configuration of the attachment member, specifically the sealed arrangement within the device, and the positioning of the magnetic coupling on a single side of the sterile field, allows for an operator to easily switch between the reusable portion (i.e., the device itself) and the disposable portion (i.e., the interchangeable tissue penetrating elements). Rather than risking breaching the field when coupling a disposable element to the reusable device, the operator need only bringing the components proximate each other, which is enough to initiate the magnetic coupling to form a completely ready-to-use device.

DETAILED DESCRIPTION

The invention generally relates to systems and methods for tissue treatment. In particular, the present invention relates to systems and methods for monitoring a status of targeted tissue undergoing a procedure via a medical device, such as, for example, a tenotomy, and further providing feedback associated with one or more parameters of the targeted tissue in real-time to thereby indicate a completeness of the procedure to an operator of the medical device.

The methods and systems according to embodiments described herein may be configured to mechanically treat a targeted area/site within a patient (human or non-human), specifically targeted musculoskeletal tissue. Treating may include, but is not limited to, puncturing, fragmenting, cutting, lysing, debriding, and any combination thereof. A targeted area may be any area of musculoskeletal tissue. For example, a targeted area/site may include but is not limited to tissue (e.g., tendons) in shoulders, elbows, knee, ankle, foot, among others, or any combination thereof. For example, the methods and systems can be used to fenestrate and release scarring or degenerate tissue in tendon, ligament, muscle, and fascia, disrupt and/or remove soft tissue calcification, debride soft tissue, cartilage, or bone, or a combination thereof.

The present invention overcomes current tissue treatment techniques by providing a system for monitoring the status of tissue at a targeted tissue site undergoing a procedure via a medical device, specifically a PNT procedure. The system is configured to detect tissue resistance as the tissue is undergoing treatment (i.e., during debridement or puncturing of the tissue). The system is configured to correlate the detected tissue resistance with a level of tissue disruption and, in turn, determine the level of completion of the procedure. The system is further configured to provide real-time feedback to an operator of the medical device during the procedure, wherein such feedback provides an indication of the level of completeness of the procedure. Accordingly, the present invention is able to provide an operator (i.e., surgeon, physician, or other medical professional) with an accurate indication of tissue disruption with each procedure, thereby ensuring that a targeted tissue site is adequately treated and the level of anticipated repair is optimal.

Figure 1A:
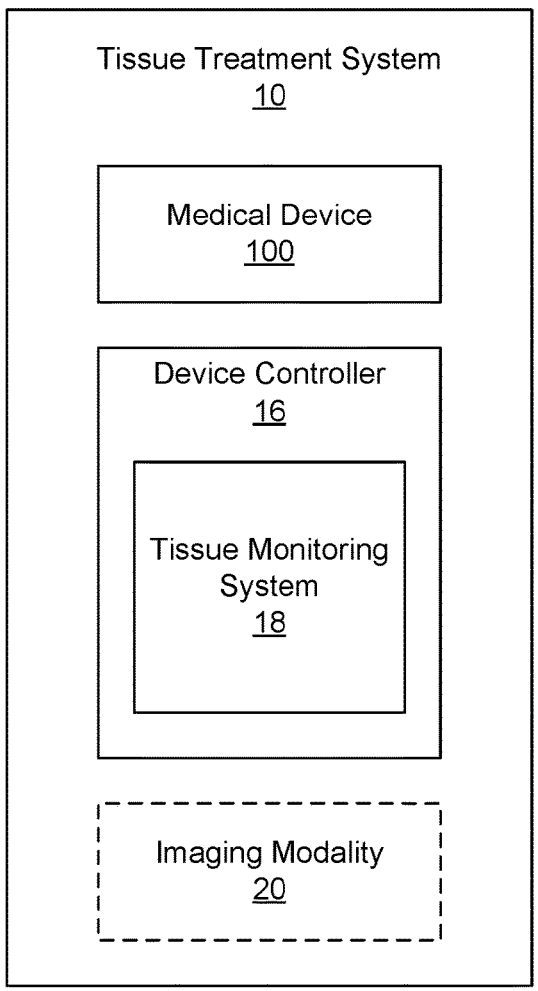
FIGS. 1A and 1B are schematic illustrations of a tissue treatment system consistent with the present disclosure.
Figure 1B:
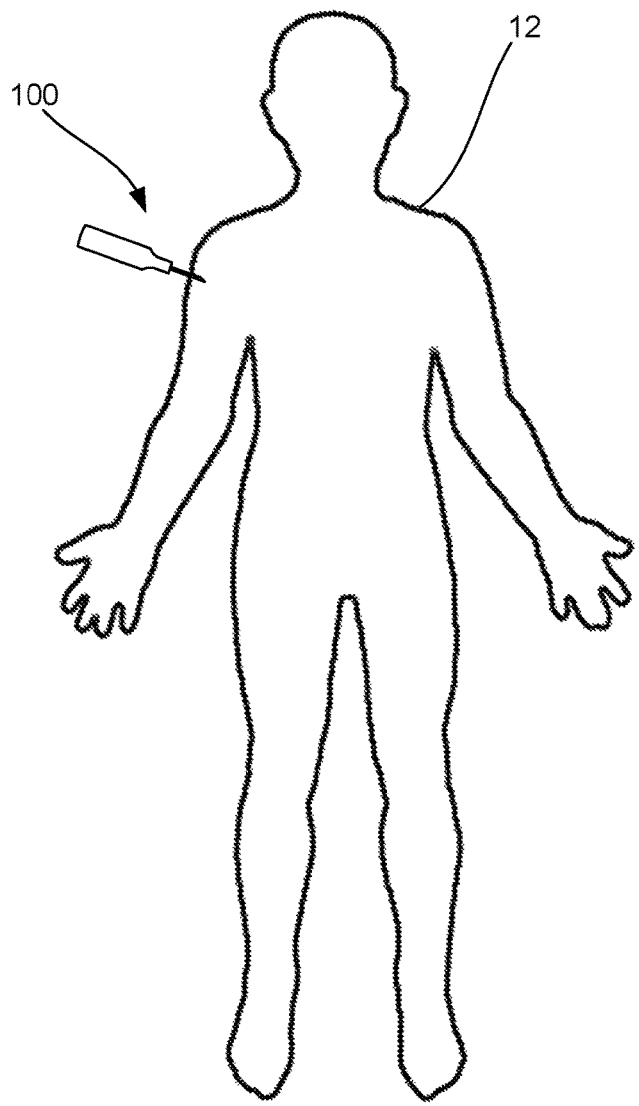

FIGS. 1A and 1B are schematic illustrations of a tissue treatment system 10 for providing treatment to a tissue site in a patient 12. The tissue treatment system 10 generally includes a medical device 100 configured to mechanically treat targeted musculoskeletal tissue. The mechanical device 100 may further be coupled to a device controller 16 to control operation of the device 100. As will be described in greater detail herein, the device controller 16 may further include a tissue monitoring system 18 configured to monitor one or more parameters of tissue currently undergoing treatment via the device 100 and, in turn, provide real-time feedback to an operator of the medical device 100 indicating a completeness of the procedure. The tissue treatment system 10 may further include an imaging modality 20. In particular, the system 10 may be used to debride, fragment, puncture, or lyse tissue in a controlled manner so as to induce a controlled injury (to thereby initiate a healing response), and the system 10 can be used in an office or ambulatory surgical suite under external or internal medical imaging modality 20, such as ultrasound, fluoroscopy, and/or other internal imaging visualization modalities.

Figure 2A:
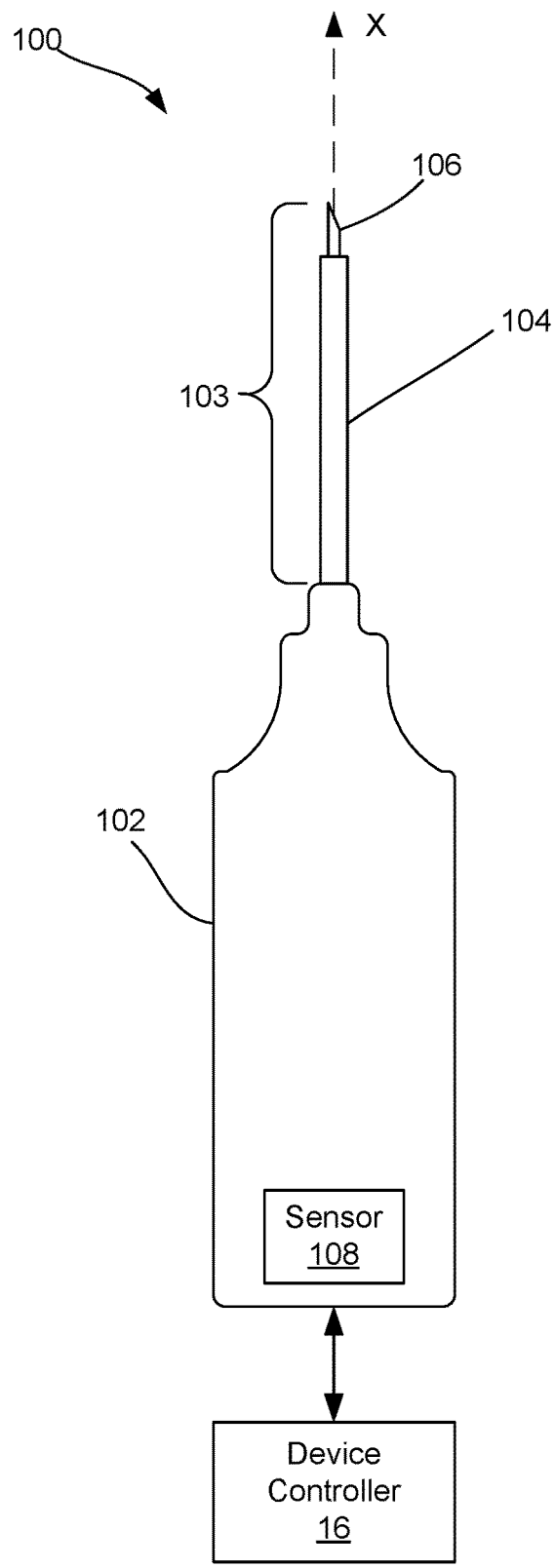
FIGS. 2A and 2B are top views of the medical device for treating a tissue site consistent with the present disclosure, illustrating the working instrument transitioning from a retracted position to an extended position.
Figure 2B:
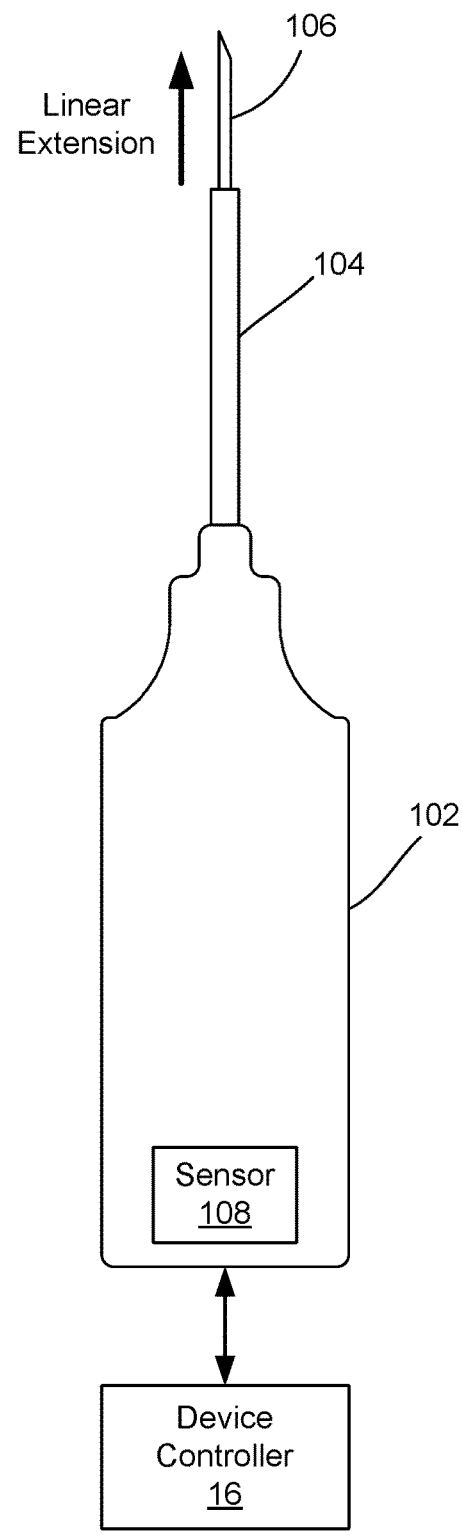

FIGS. 2A and 2B are top views of the medical device for treating a tissue site consistent with the present disclosure, illustrating the working instrument transitioning from a retracted position to an extended position. The medical device 100 may be in the form of a handheld device, which includes body 102, generally shaped and adapted for manual manipulation. For example, in some embodiments, the body 102 may be ergonomically configured to fit within the user's hand and may include contoured surfaces to facilitate grasping by the user. As will be described in greater detail herein, the body 102 may include an interior cavity configured to house and enclose multiple components within. Thus, the body 102 may be of a multi-component construction (i.e., two-part, three-part, etc., construction), such that the interior of the body 102 may be accessed. The body 102 may include proximal end, a distal end, and a length therebetween. The body 102 may also include a longitudinal axis X extending in a direction parallel to its length from the proximal to the distal end.

The medical device 100 further includes an instrument assembly 103 coupled to the body 102, the instrument assembly including a guide member 104 and a working instrument 106, a portion of which is housed within the body 102. The working instrument 106 includes a distal tip configured to treat a target tissue site (i.e., puncture, fragment, cut, debride, etc. the tissue). As shown, the working instrument 106 is in the form of a needle. For example, the working instrument 106 may include a hollow or solid needle, which may include a distal tip having a sharp point, one-sided serrated edge, a blunt point, a ball shape at the end (e.g., a mace), textured and/or granulated surface, a tapered point, a flat edge/end, a pointed tip, a bur tip, or a combination thereof. However, it should be noted that the working instrument 106 could be in any form so as to appropriately treat a target tissue as intended.

The guide member 104 is coupled to the body 102 and generally extends from the distal end thereof. The guide member 104 may generally be configured to provide the working instrument 106 with access to a targeted tissue area. The guide member 104 may be configured to provide a stabilizing path to the targeted tissue area for the working instrument 106. In particular, the guide member 104 may have an elongated tubular shape, for example, such as a cannula, with a circular cross-section. The guide member 104 may be configured to be stationary when attached to the body 102 and the working instrument 106 may be configured to linearly move within the guide member 104 generally along the longitudinal axis X of the body 102 between one or more fixed distances when transitioning between an retracted and extended positions during treatment.

The body 102 may include one or more receiving members for the instrument assembly 103. For example, in some embodiments, the body 102 may include one or one receiving members disposed about the distal end, such as a self-contained opening and/or slot configured to receive one or more attachment members of the instrument assembly 103. In the embodiments described herein, the instrument assemblies may be coupled to the body by way of one or more corresponding attachment members provided within the body and configured to retain at least a portion of the proximal ends of the guide member and/or working instrument.

The device 100 may further include a sensor 108. The sensor 108 may be operably coupled to the working instrument 106 when coupled to the body 102, or may be coupled to other components of the device, such as a motor of the device configured to oscillate the working instrument 106, as will be described in greater detail herein. The sensor 108 may generally be configured to directly or indirectly sense/measure tissue resistance during the procedure (i.e., resistance to puncturing or debridement from the distal tip of the working instrument 102). More specifically, the sensor 108 may be configured to sense a various parameters associated with components of the device 100 during operation thereof and related to a resistance of the tissue, including, but not limited to, a pressure force associated with the tissue, an electrical current associated with operation of the motor, an output of the motor associated with a rotation speed of a drive shaft of the motor, and the like. Accordingly, the feedback sensor 108 may include a piezoelectric sensor, a current sensor, and/or a tachometer or rotary encoder, for example. Thus, the sensor 108 may be able to sense resistance exerted upon the working instrument when the working instrument transitions from the retracted position to the extended position and engages tissue. As will be described in greater detail herein, sensor 108 may be configured to transmit signals associated with the tissue resistance to the tissue monitoring system 18 for further processing.

Figure 3:
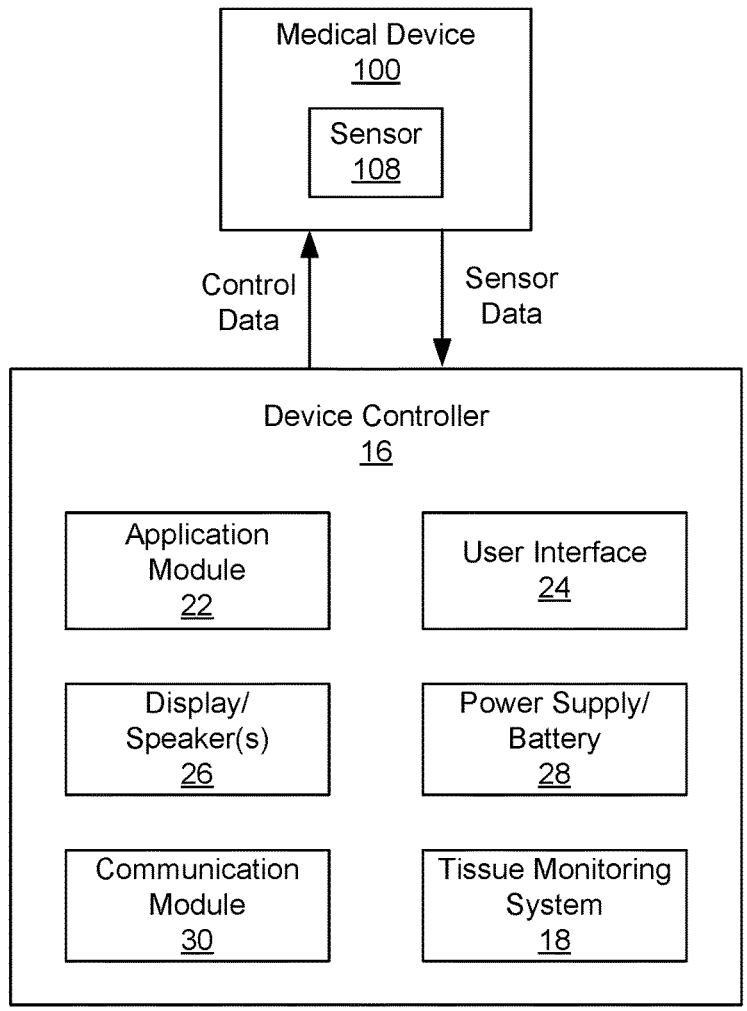
FIG. 3 is a block diagram illustrating the controller and tissue monitoring system consistent with the present disclosure.
Figure 4:
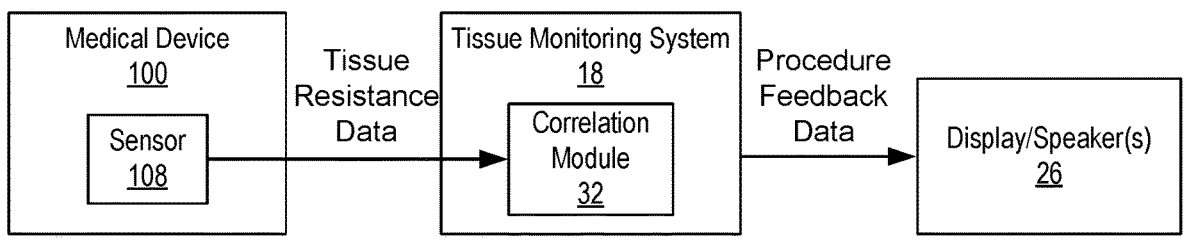
FIG. 4 is a block diagram illustrating the tissue treatment system, specifically the communication and exchange of data between the medical device and the tissue monitoring system.

FIG. 3 is a block diagram illustrating the controller 16 and tissue monitoring system 18 consistent with the present disclosure. FIG. 4 is a block diagram illustrating the tissue treatment system 10, specifically the communication and exchange of data between the medical device 100 and the tissue monitoring system 18.

As shown, the system 10 includes a controller 16, which may be configured to control operation of the device 100, specifically control movement of the working instrument 106 (via transmittal of control data) and further receive sensor data, in the form of signals, from the sensor 108, wherein the sensor data is generally associated with the working instrument 106 and the corresponding tissue undergoing treatment. The controller 16 may be incorporated as part of the device 100 itself (i.e., controller components integrated into the body 102 of the device 100) or may be directly coupled to the device by a wired or wireless connection. The controller 16 may include an application module 22, a user interface 24, a display and/or speakers 26, a power supply 28, such as batteries (single use or rechargeable), a communication module 30, and the tissue monitoring system 18. Accordingly, the controller 16 may include a computing processor, one or more computing applications, and memory for storing the one or more computing applications and/or one or more sets of software instructions for carrying out various functions of the tissue treatment system, as described herein. For example, the software application 22 may include all functions and applications of the system 10, such as instructions for performing the various tasks and other functionalities of performing the tissue treatment as described herein. The user interface 24 may allow for the receipt of user input to control the device 100, such as switches, buttons, triggers, or other means of input for controlling the movement of the working instrument 106, such as an on button, an off button, and input for controlling the speed of movement of the working instrument 106 and/or a timer-controlled movement (i.e., movement of the working instrument 106 over a pre-programmed period of time). The controller 16 may also include a display and/or speakers for providing real-time feedback to the operator of the device indicating the level of completeness of the procedure and/or parameter(s) of the tissue undergoing treatment, as generated by the tissue monitoring system 18. The communication module 30 may allow for wireless and/or wired communication between the controller 16 and the device 100 (if the controller 16 is not incorporated directly into the device 100 itself) as well as communication with other electronic devices, such as other computing devices in the procedure room.

The tissue monitoring system 18 may be configured to receive signals from a sensor 108 coupled to the working instrument. As previously described, the sensor 108 may generally be configured to directly or indirectly sense/measure tissue resistance during the procedure (i.e., resistance to puncturing or debridement from the distal tip of the working instrument 106). Accordingly, in one embodiment, the sensor 108 may include a pressure sensor, such as a piezoelectric sensor for example. Additionally, or alternatively, the sensor 108 may include a current sensor configured to sense an electrical current associated with operation of the motor, which can indicate a resistance of the tissue to penetration. Additionally, or alternatively, the sensor 108 may include a tachometer or rotary encoder configured to sense an output of the motor associated with a rotation speed of a drive shaft of the motor, and the like, which can indicate a resistance of the tissue to penetration.

In turn, the tissue monitoring system 18 is configured to receive signals from the sensor 108, wherein the signals include data associated with a resistance of the tissue during the procedure. The tissue monitoring system 18 includes a correlation module 32 configured to correlate the tissue resistance data with a level of tissue disruption, and subsequently determine the level of completion of the procedure. The correlation module 32 may include custom, proprietary, known and/or after-developed statistical analysis code (or instruction sets), hardware, and/or firmware that are generally well-defined and operable to receive two or more sets of data and identify, at least to a certain extent, a level of correlation and thereby associate the sets of data with one another based on the level of correlation. In particular, evidence suggests that the effectiveness of the procedure is related to the degree of tissue disruption, such that it has been found that there is a perceivable decrease in tissue resistance (i.e., decrease to puncture resistance) as the level of tissue disruption increases. Accordingly, tissue resistance and tissue disruption have an inverse relationship. For example, as tissue resistance decreases, tissue disruption increases. The analysis of tissue resistance data in order to determine completeness of a procedure may vary depending on particular attributes of an individual patient, such that gender, age, body mass index, health-related characteristics (i.e., weight, body mass index, smoking, diseases, etc.), and the like may play a role in the analysis. For example, males between the ages of 20 and 30 years old may have a specific range of acceptable tissue resistance and thus any patient within this category (i.e., male between age 20 and 30) will share a common variable.

The tissue monitoring system 18 is further configured to generate and provide feedback data to an operator of the medical device (via the display 26 or other means) based on the received tissue resistance data. In particular, the feedback data may relate to one or more parameters associated with the procedure, including actual number values and/or a scaled readout of tissue resistance, power required to overcome tissue resistances, force to overcome tissue resistance, and the like. Furthermore, in some embodiments, the output of the feedback data may include an indication of the level of completeness of the procedure (i.e., a percentage of total completion based on a 100 percent scale).

Figure 5:
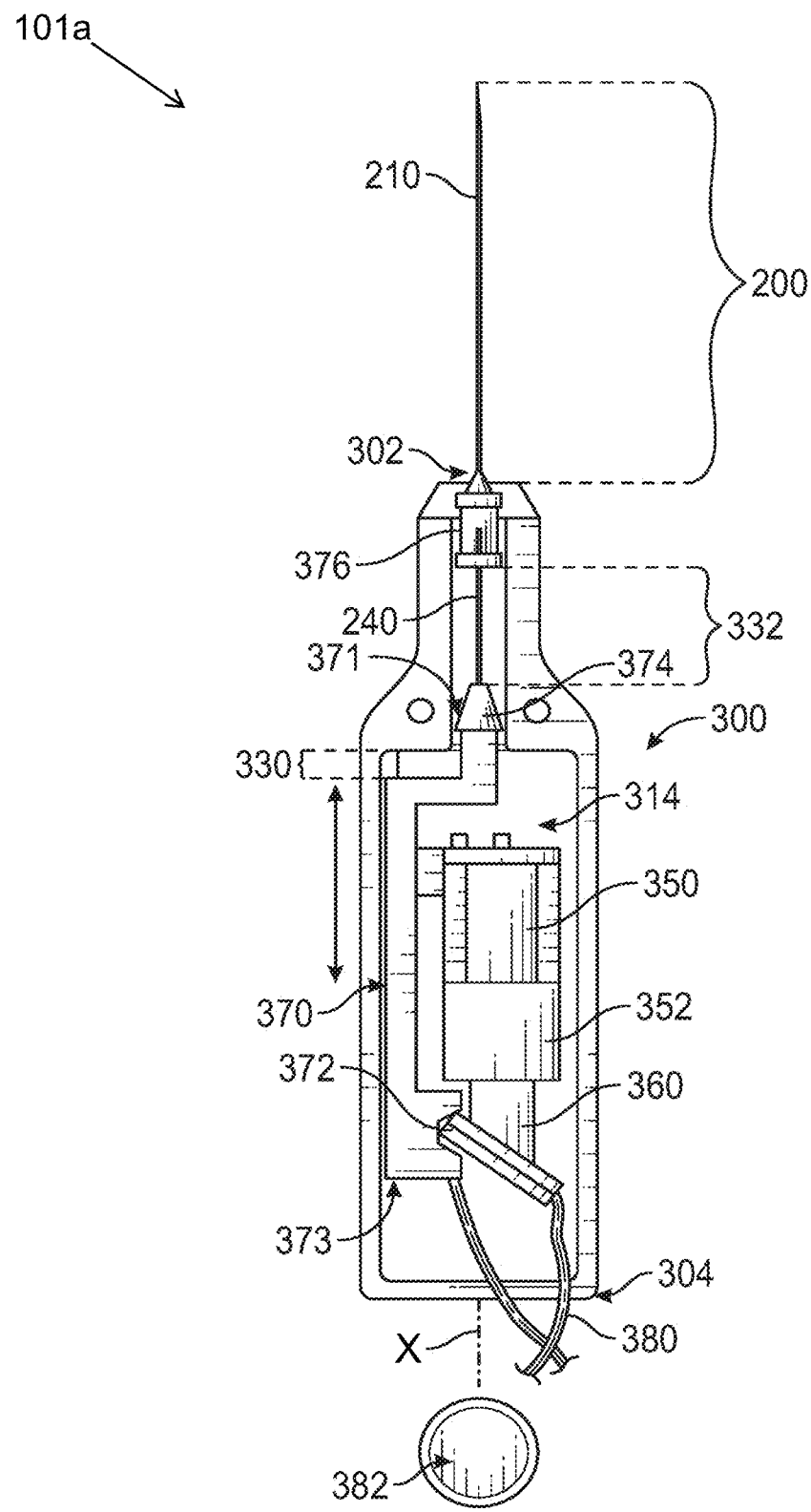
FIG. 5 is a side view, partly in section, of a first embodiment of a medical device of FIG. 2 consistent with the present disclosure.
Figure 6:
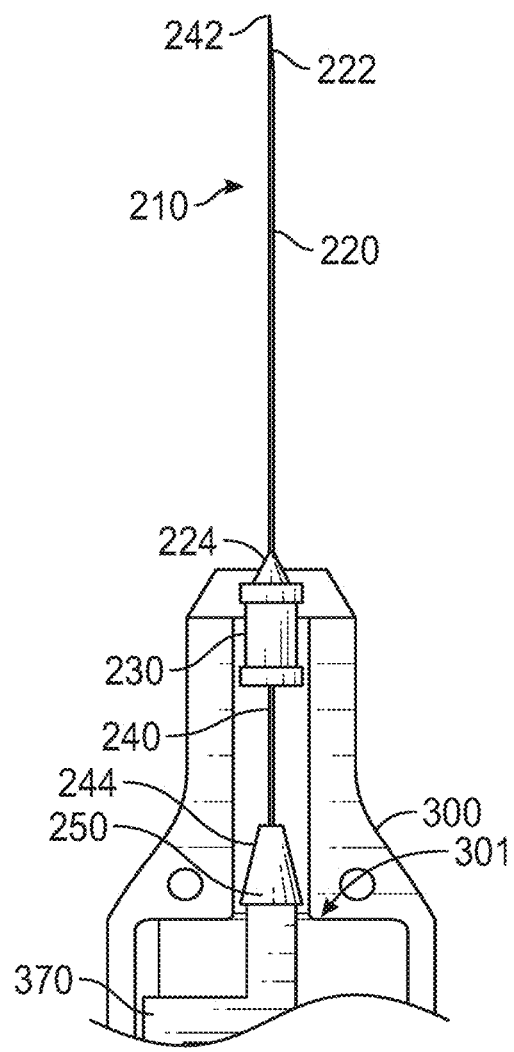
FIG. 6 is an enlarged side view of a distal portion of the medical device of FIG. 5 to illustrate further detail.

FIG. 5 is a side view, partly in section, of a first embodiment of a medical device 100a consistent with the present disclosure. FIG. 6 is an enlarged side view of a distal portion of the medical device 100a of FIG. 5 to illustrate further detail.

The instrument assembly 200 may include an instrument guide 210 configured to provide access to a targeted tissue area and an instrument 240. The instrument guide 210 may be configured to provide a stabilizing path to the targeted tissue area for an instrument when attached to the body 300. The instrument guide 210 may be configured to be stationary when attached to the body 300 and the instrument 240 may be configured to linearly move within the instrument guide 210 to one or more fixed distances. In this way, the instrument 240 can be moved without moving the instrument guide 210. Thus, the instrument guide 210 can control the disruption to the targeted area by preventing the disruption of the surrounding tissue by the instrument guide 210 and/or the instrument 240.

The instrument guide 210 may include an instrument guide member 220 having a first (exposed) end 222, a second end 224, and a length there between. The length of the instrument guide member 220 may vary and for example, may depend on the instrument to be guided, the target area to be treated, among others, or a combination thereof. In some embodiments, the instrument guide member 220 may have an elongated tubular shape, for example, such as a cannula. In some embodiments, the instrument guide member 220 may have a circular cross-section. In other embodiments, the instrument guide member 220 may have a different cross-section, such as rectangular or triangular.

The instrument guide member 220 may be configured to directly penetrate tissue to access the target area. In some embodiments, the instrument guide member 220 may include a tip configured to penetrate tissue. In some embodiments, the end 222 may include a sharp tip. The tip may include but is not limited to a pointed tip, tapered tip, blunt tip, as well as others. In other embodiments, the end 222 may have a different tip.

The instrument 240 may include a first end 242, a second end 244, and a length there between. The length of the instrument 240 may vary and for example, may depend on the length of the instrument guide member 220, the target area to be treated, among others, or a combination thereof. In some embodiments, the instrument 240 may be the same, shorter, and or longer than the instrument guide 210.

The instrument 240 may be any instrument configured to treat tissue. The instrument 240 may include but is not limited to an instrument configured to disrupt, debride, decorticate, fragment, or a combination thereof. Additionally, or alternatively, the instrument 240 may be configured to puncture or pierce tissue. For example, the instrument 240 may include one or more hollow and/or solid needles. In some embodiments, the needles may include on the first end 242 and/or along a portion of the length a sharp point, one-sided serrated edge, a blunt point, a ball shape at the end (e.g., a mace), textured and/or granulated surface, a tapered point, a flat edge/end, a pointed tip, a bur tip, among others, or a combination thereof.

The instrument assembly 200 may include one or more attachment members configured to removably attach the instrument assembly 200 to the body 300. For example, in some embodiments, the instrument guide 210 and/or the instrument 240 may include an attachment member and thus may each be configured to be separately removable from the body 300 and/or the instrument assembly 200. For example, as shown in FIG. 6, the instrument guide 210 may include an attachment member 230 disposed at the end 224 and the instrument 240 may include an attachment member 250 disposed at the end 244. The attachment members 230 and 250 may be the same or different. For example, the attachment members 230 and/or 240 may include a hook, a plug, a magnet, a luer lock, among others, or a combination thereof. In some embodiments, the attachment members 230 and/or 240 may include an opening. For example, as shown in FIG. 6, the attachment member 230 may include an opening through which the instrument 240 may linearly move.

The instrument assembly 200 may include an attachment member configured to removably attach the instrument assembly 200 (e.g., at least the instrument guide and the instrument) to the body 300. For example, the instrument assembly 200 may include a housing in which the instrument guide 210 and/or the instrument 210 may be included so that the instrument assembly 200 is self-contained and encased. In this example, at least the housing may include an attachment member configured to removably attach the instrument assembly to the body. In some embodiments, the instrument guide 210 and/or the instrument 240 may additionally be configured to be separately removable from the instrument assembly 200. For example, the instrument guide 210 and/or the instrument 240 may be configured to be removed from the housing and/or each other. By way of example, the instrument guide 210 may be configured to be removable from the instrument assembly 200, the instrument 240 and/or body 300 so that the instrument guide 240 can remain in the patient after being used. In this example, the instrument guide 240 may be configured to deliver therapeutic agent(s) to the site.

The body 300 may include a first end 302, a second end 304, and a length there between. The body 300 may also include a longitudinal axis X that is parallel to its length. In some embodiments, the body 300 may include one or more inner compartments disposed along the length for one or more components of the medical device 100a.

As shown in FIG. 6, the medical device 100a may include an actuator 350 disposed in the body 300 and configured to cause the instrument 240 to linearly oscillate within the guide member 220 so that the instrument 240 extends past the (exposed) end 222 one or more fixed distances. The fixed distance can correspond to the maximum length that the instrument 200 is exposed past the instrument guide (e.g., the maximum distance between the end 242 of the instrument and end 22 of the instrument guide). In some embodiments, the actuator 350 may be a motor.

The medical device 100a may include a rotatable drive shaft 352 disposed adjacent to the actuator 350. In some embodiments, the body 300 may include an inner compartment 314 in which the actuator 350 and the rotatable drive shaft 352 may be fixedly disposed.

The medical device 100a may include at least one rotatable member 360 disposed in the body 300 on the rotatable drive shaft 352 of the actuator 350. In some embodiments, the rotatable member 360 may be a barrel cam. As shown in FIG. 5, the rotatable member 360 may be a radial/disc cam tilted at a defined angle with respect to the actuator. In some embodiments, the rotatable member 360 may be another type of cam. For example, the rotatable member 360 may be a curved disc, cylindrical cam, a drum cam, a globoidal cam, among others, or a combination thereof. In other embodiments, the at least one rotatable member 360 may be one or more gears.

The medical device 100a may include a linear oscillating member 370 disposed in the body 300 and configured to move linearly with respect to the length of the body 300. In some embodiments, the linear oscillating member 370 may be an elongated shaft. In some embodiments, the linear oscillating member 370 may include a first end 371, a second end 373, and a length there between. In some embodiments, the linear oscillating member 370 may be disposed within the body 300 so that it extends from the rotatable member 360 between the instrument 240 and/or the instrument guide 220.

The linear oscillating member 370 may include one or more receiving members configured to receive the rotatable member 360. As shown in the FIG. 6, the linear oscillating member 370 may include a receiving member 372 for the rotatable member 360. As shown in FIG. 5, the receiving member 372 may be disposed near the end 373. In some embodiments, the receiving member 372 may be a slot and/or aperture configured to receive the rotatable member 360 and in which the rotatable member 360 may rotate. When the rotatable member 360 is disposed in the receiving member 372, the rotatable member 360 may be configured to transform the rotary motion of the actuator 350 via the rotatable member 360 to cause the instrument 240 to linearly oscillate.

In operation, the actuator 350 may be configured to rotate 360° (e.g., make full revolutions) to cause the linear oscillating member 370 to move in a linear, oscillating manner. In other embodiments, in operation, the actuator 350 may be configured to rotate a partial revolution (e.g., rotate less than rotate 360°) and reverse rotation direction when the actuator 350 reaches the end of the partial revolution in that direction to cause the linear oscillating member 370 to move in a linear, oscillating manner via the linear oscillating member 370.

The body 300 may include one or more receiving members for the instrument assembly 200. In some embodiments, the body 300 may include one or one receiving members disposed about the first end 302. For example, the body 300 may include a self-contained opening and/or slot configured to receive one or more attachment members of the instrument assembly 200. In this example, the instrument assembly 200 may be encased and may include one or more attachment members on the bottom (e.g., the side opposite the exposed end of the instrument guide 220).

The one or more receiving members for the instrument assembly 200 may be disposed within the one or more inner compartments of the body 300. In some embodiments, the linear oscillating member 370 may include a receiving member 374 configured to receive the tool 240. In some embodiments, the receiving member 374 may be disposed about the end 374. In some embodiments, the receiving member 374 may be disposed within the linear oscillating member (see FIG. 5). In some embodiments, the body 300 may include a receiving member 360 for the instrument guide 210.

The body 300 may be ergonomically configured to fit within the user's hand. In some embodiments, the body 300 may include contoured surfaces to facilitate grasping by the user. In some embodiments, the body 300 may include a trigger member configured to directly or indirectly cause the actuating member 350 to be activated (i.e., powered). For example, the trigger member may be a button or a mechanical switch configured to directly activate the actuating member 350. In some embodiments, the button or mechanical switch may be disposed on the body 300 to ergonomically align with a user's thumb or other fingers when the body 300 is held in the user's hand.

The body 300 may include additional and/or alternative buttons or switches. For example, the body may include a dial or press a button configured to adjust the fixed distance of the instrument 240. In another example, the body 300 may include a dial or press a button configured to adjust the speed of the linear oscillation of the instrument 240. In a further example, the body 300 may include a button to control the position of the instrument with respect to the instrument guide (e.g., when the power to the actuator is stopped). In this example, the button may be configured to cause the actuator to move so that the instrument is retracted within the instrument guide. In some embodiments, the actuator 350 may cause the instrument 240 to retract within the instrument guide member 220 when the actuating member 350 is deactivated.

The trigger member may be a foot-operated switch that is either electrically connected to the body 300 or wirelessly coupled to the body 300 (e.g., via blue-tooth communication technology). In some embodiments, a computer that is either electrically connected to the body 300 or wirelessly coupled to the body 300 may be configured to control and/or activate the actuating member 350. In some embodiments, the foot-operated switch and/or computer may control one or more output functions (e.g., speed, fixed distance, or the like) in addition to and/or in the alternative to the controls being located on the body 300.

The medical device 100a may include a power source 380. The power source 380 may be any source configured to provide electrical power to the body 300. For example, the power source 380 may be configured to directly or indirectly deliver power to the actuator 350. In some embodiments, the power source 380 may be a battery 382 disposed within an inner compartment of the body 300. The battery 280 may be rechargeable and/or replaceable. In some embodiments, the power source 280 may be an external source, such as a power supply or wall socket, or a combination thereof.

As shown in FIG. 6, the actuator 350 may be disposed between the rotatable member 360 and the instrument 240. The linear oscillating member 370 may be disposed adjacent to the actuator 350 so that the linear oscillating member 370 extends along the length of actuator from about the rotatable member 360 and the instrument assembly 200. In this way, the body 300 may have a more compact and narrower design.

In operation, the actuator 350 may be configured to control, the instrument 240 so that it linearly oscillates a fixed distance (i.e., the length of the exposed instrument 200 past the instrument guide member 220 at end of oscillation (e.g., the maximum distance between the end 242 of the instrument 240 and the end 222 of the instrument guide 210)). In this way, the instrument can repeatedly puncture and/or fenestrate and/or pierce the target tissue. In some embodiments, the fixed distance may be based on the angle and/or rotation of the rotatable member, the distance between the instrument guide, the instrument, and/or body (e.g., linear oscillating member (see area 332), and/or the distance between the linear oscillating member and the inner compartment (e.g., area 330).

The medical device 100a may be configured to oscillate one or more fixed distances. For example, the fixed distance may be set by the user. The body 300 and/or instrument assembly 200 may be configured to set one or more fixed distances for which the instrument 240 may repeatedly move. For example, the fixed distance may correspond to the distance between the instrument 240 and instrument guide 210 selected by the user on the instrument assembly 200, the angle and/rotation of the rotatable member 370, or a combination thereof.

In operation, the actuator 350 (e.g., via the linear oscillating member 350) can cause the instrument 240 to repeatedly move linearly between a forward position (away from the body 300) and a backward position (towards the body 300) along the longitudinal axis X of the body with respect to the instrument guide member 220 and/or body 300. In the forward position, the instrument 240 may extend a fixed distance beyond the instrument guide member 220 and therefore a portion of the instrument 240 corresponding to the fixed distance may be exposed to treat the tissue. In the backward position, the instrument 240 may be disposed within the instrument guide member 230, instrument assembly 200, and/or a self-contained portion of the body 300. In some embodiments, the instrument 240 may be configured to be disposed in a resting position. In this way, although the instrument assembly 200 may be exposed to tissue and bodily fluid, the components of the body 300 may remain sterile.

To activate the actuator 350, a user may press a triggering member (e.g., power button) to cause the actuator 350 to rotate thereby causing the rotatable member 360 to rotate (via the rotatable drive shaft 352). The rotatable member 360 and actuator 350 may be disposed so that the rotation motion is about the longitudinal axis X of the body 300. The rotation motion of the rotatable member 360 can then cause the linear oscillating member 370 to linearly oscillate along the central axis X (e.g., repeatedly move forward/backward with respect the length of the device). The linear oscillating member 370 can then transfer the linear motion to the instrument 240. The instrument 240 can be configured to linearly oscillate within the stationary instrument guide member 220. In some embodiments, the backward and forward positions of the instrument 240 with respect to the instrument guide member may be configured to depend on the angle of the portion of the rotatable member 360 that is disposed within the linear oscillating member 370.

Figure 7:
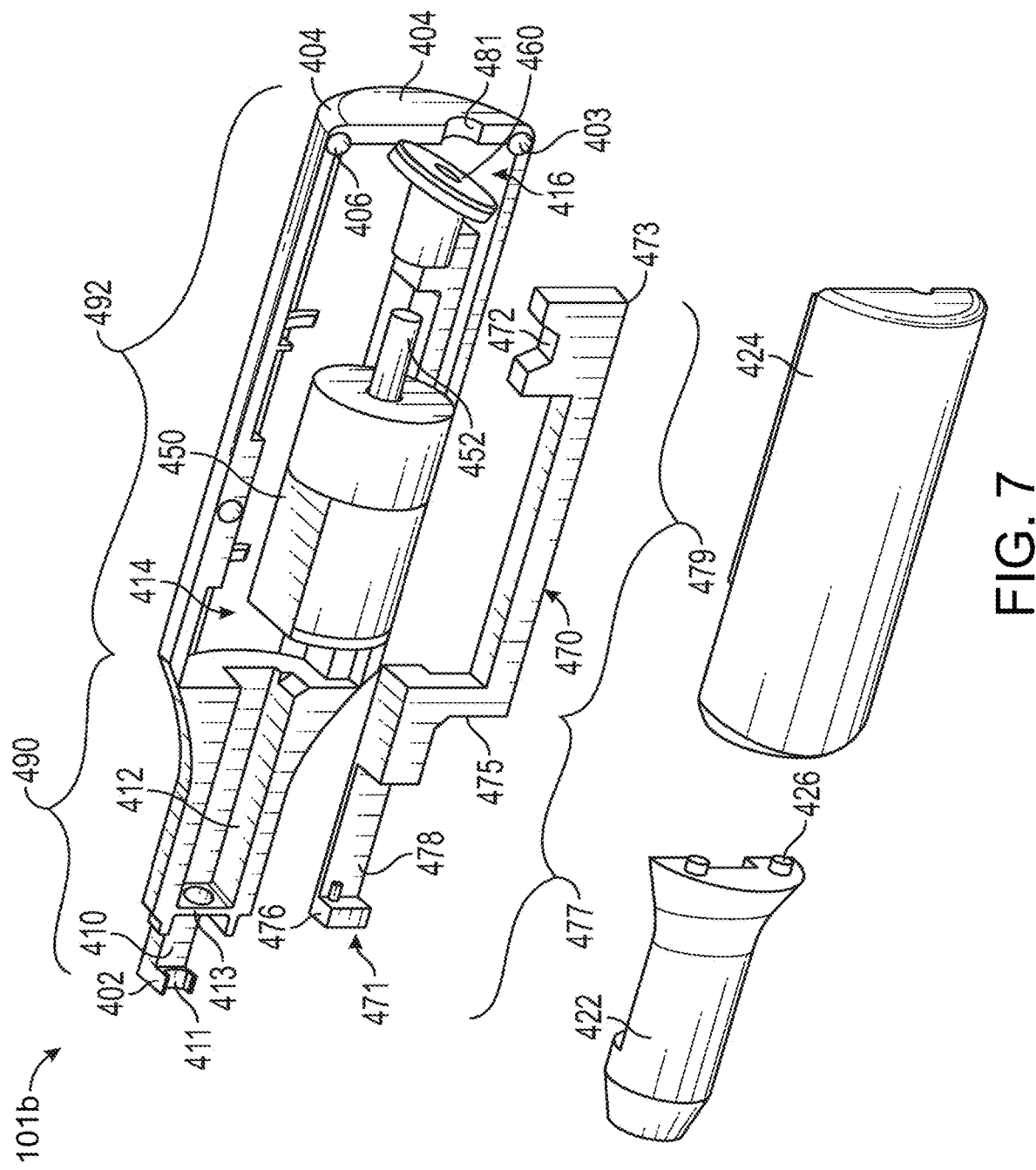
FIG. 7 is a partial, exploded view of a second embodiment of a medical device of FIG. 2 consistent with the present disclosure.

FIG. 7 is a partial, exploded view of a second embodiment of a medical device 100b consistent with the present disclosure. It is understood that the embodiments of the instrument assembly 200 described with respect to FIGS. 5 and 6 may also be used with the device shown in and described with respect to FIG. 7. It is understood that the embodiments of the body, actuator, rotatable member, and linear oscillating member, described with respect to FIGS. 5 and 6 may also apply to the body, actuator, rotatable drive shaft, rotatable member, and linear oscillating member described with respect to FIG. 7, and vice versa. The body, actuator, rotatable drive shaft, rotatable member, and linear oscillating member described with respect to FIG. 7 may be similar with some respects to the body, actuator, rotatable drive shaft, rotatable member, and linear oscillating member described with respect to FIGS. 5 and 6.

Like body 300 of medical device 100a, the body 400 of medical device 100b may have a first end 402, a second end 404, and a length there between. In some embodiments, the body 400 may include one or more sections, including a first section 490 and a second section 492. In other embodiments, the body 400 may include more or less sections.

Like the medical device 100a, the medical device 100b shown in FIG. 7 may include an actuator 450 including a rotatable shaft 452, a rotatable member 460, and a linear oscillating member 470. The actuator 450 may be configured to rotatably drive the rotatable member 460, which in turn causes the linear oscillating member 470 to linearly oscillate (i.e., repeatedly move in a backward and forward manner).

As shown in FIG. 7, the linear oscillating member 470 may include a first end 471, a second end 473, and a length there between. In some embodiments, the linear oscillating member 470 may include one or more sections. In some embodiments, the linear oscillating member 470 may include a first section 477 and a second section 479. In some embodiments, the first section 477 may include a portion of the linear oscillating member 470, for example, from first end 471 to intermediary area 475, and the second section 479 may include a portion of the linear oscillating member 470, from the intermediary area 475 to the second end 475. In some embodiments, like the oscillating member 370, the oscillating member 470 may include a receiving member 472 configured to receive the rotatable member 460. The receiving member 472 may be configured so that the rotatable member 460 may be rotate within the receiving member 472.

In other embodiments, the body 400 may include one or more inner compartments configured to receive the actuator 450, the rotatable shaft 452, a rotatable member 460, and the linear oscillating member 470. For example, the body 400 may include a first inner compartment 412 to receive the instrument assembly 200 and/or a portion of the linear oscillating member 470, a second inner compartment 414 to receive a portion of the linear oscillating member 470, the actuator 450, and/or the rotatable member 460, and a third inner compartment 416 to receive a power source. The inner compartment 412 may be disposed in the first section 490 and the inner compartments 414 and 410 may be disposed in the second section 492. The actuator 450 and the second section 479 may be disposed in the inner compartment 414 so that the actuator 450 is disposed within the length of the second section 479.

The linear oscillating member 470, the actuator 450, and the rotatable member 416 may be fixedly disposed within the inner compartments. The instrument assembly 200 and/or the power source may be fixedly disposed within the inner compartments. In other embodiments, the instrument assembly 200 and/or the power source may be removably disposed within the inner compartments. For example, the body 400 may be a reusable device and the instrument assembly 200 may be replaced for each use. In another example, the power source may be a replaceable battery. In these examples, the inner compartments that are configured to be accessible to replace the instrument assembly 200 and/or power source may be self-contained so as not to contaminate the other inner compartments.

The first section 490 may be configured to communicate with the instrument assembly 200. For example, in some embodiments, the first section 490 may be configured to directly and/or indirectly receive the instrument assembly 200. By way of example, the first section 490 and/or the linear oscillating member 470 may be configured to receive the instrument assembly 200. The body 400 may include a receiving member 410 (e.g., an inner compartment) to receive an instrument guide 210. When the instrument guide 210 is disposed in the receiving member 410, the receiving member 410 may be configured to fixedly dispose the instrument guide 210 so that it is stationary while the instrument 240 is moving.

The linear oscillating member 470 may include a receiving member 478 configured to receive the instrument 240. When the instrument 240 is disposed in the receiving member 478, the instrument 240 may move with the linear oscillating member 470. The linear oscillating member 470 may include an opening and/or channel 476 through which an instrument may be disposed so that it can extend through the body 400.

The body 400 may be configured so that the instrument assembly 200, instrument guide 210 and/or the instrument 240 may be removed after use. The body 400 may also include an opening and/or aperture 411 through which the instrument guide 210 and/or instrument 240 may extend through the body.

In some embodiments, the receiving members 410 and/or 478 may be omitted. For example, the opening and/or aperture 411 may be configured to receive and communicate with an encased instrument assembly 200 so that the linear oscillating member 470 can cause the instrument 210 to linearly oscillate.

The body 400 may include one or more cases configured to cover the one or more inner compartments. In some embodiments, the one or more cases may be configured to be removably attached. As shown in FIG. 7, the body 400 may include cases 422 and 424. For example, the case 422 may be configured to be fixed to the body 400 to cover the first section 490 and the case 424 may be configured to be removable attached to cover the second section 492. The case 422 may include one or more attachment members 426 configured to attach the case 422 to the case 424 and the case 424 may include complimentary receiving members. In some embodiments, the body 400 may include complementary receiving members 406 configured to receive the case 422 and/or the case 424. The attachment members, for example, may be a protruding member and the receiving members may be holes. In other embodiments, the one or more attachment members may be different. For example, the one or more attachment members may be magnetic, hook, luer lock, among others. In other embodiments, the body may include one case that may be configured to be fixed and not removable by the user.

Figure 8:
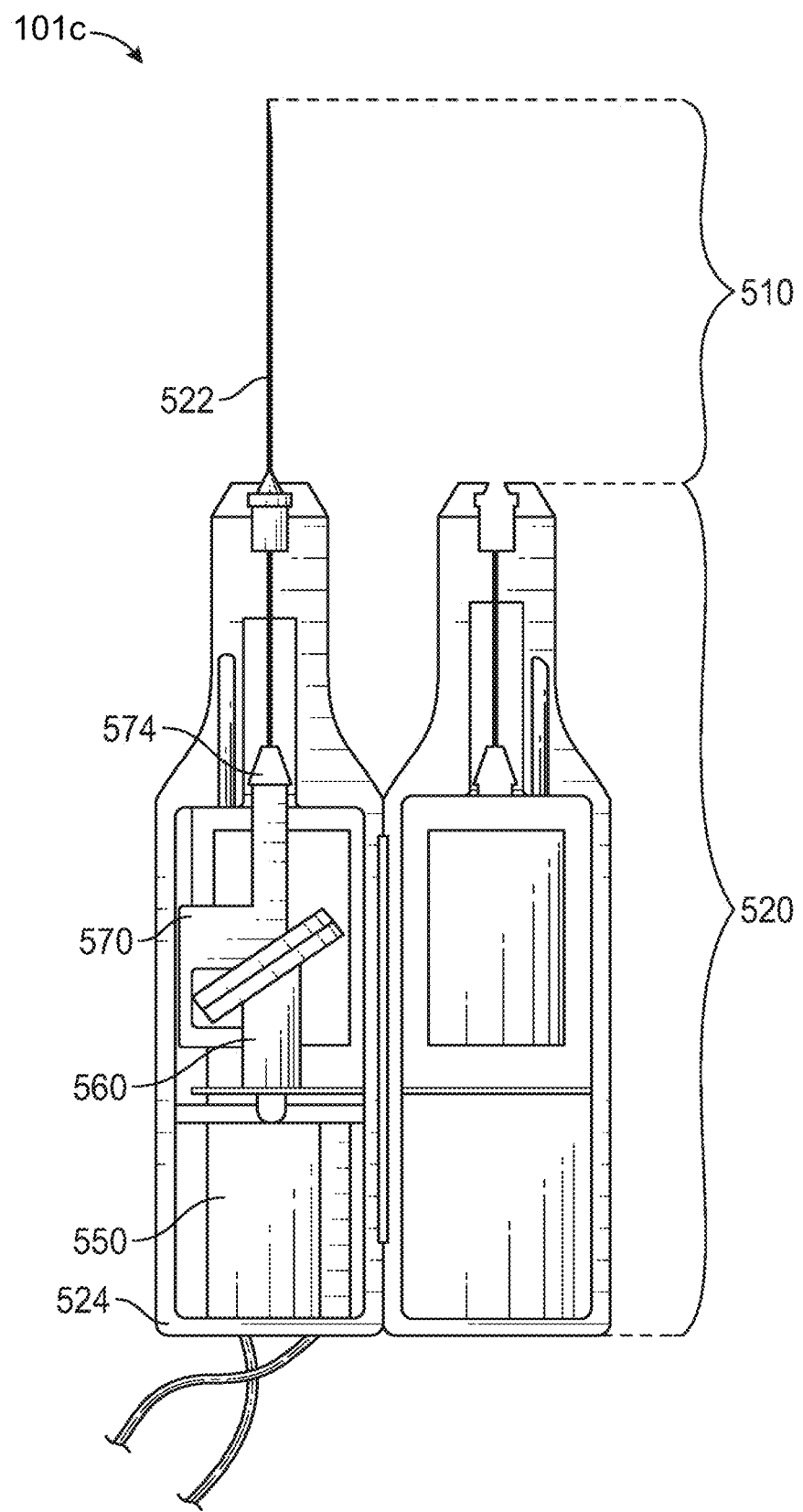
FIG. 8 is a side view, partly in section, of a third embodiment of a medical device of FIG. 2 consistent with the present disclosure.

FIG. 8 is a side view, partly in section, of a third embodiment of a medical device 100c consistent with the present disclosure. It will also be understood that the configurations of body, actuator, rotatable member, and linear oscillating member, shown in FIGS. 5-7 are not limited to those shown in the figures and may include other configurations. For example, these components disposed in a different configuration, as shown in FIG. 8. As shown in FIG. 8, a medical device 100c may include an instrument assembly 510 and a body 520. Like the body 300, the body 500 has a first end 522, a second end 524, and a length there between. The body 300 may include an actuator 550, a rotatable member 560, and a linear oscillating member 570. The medical device 100c is similar to the medical device 100a but for the locations of the actuator 550, the rotatable member 560, and the linear oscillating member 570. As shown in FIG. 8, the rotatable member 360 may be disposed between the instrument assembly 200 and the actuator 550. In this example, the linear oscillating member 570 can have a shorter length because the actuator 550 can be disposed not along the length. The system 500 may operate in a similar fashion as the system shown and described with respect to FIGS. 5-7.

Figure 9:
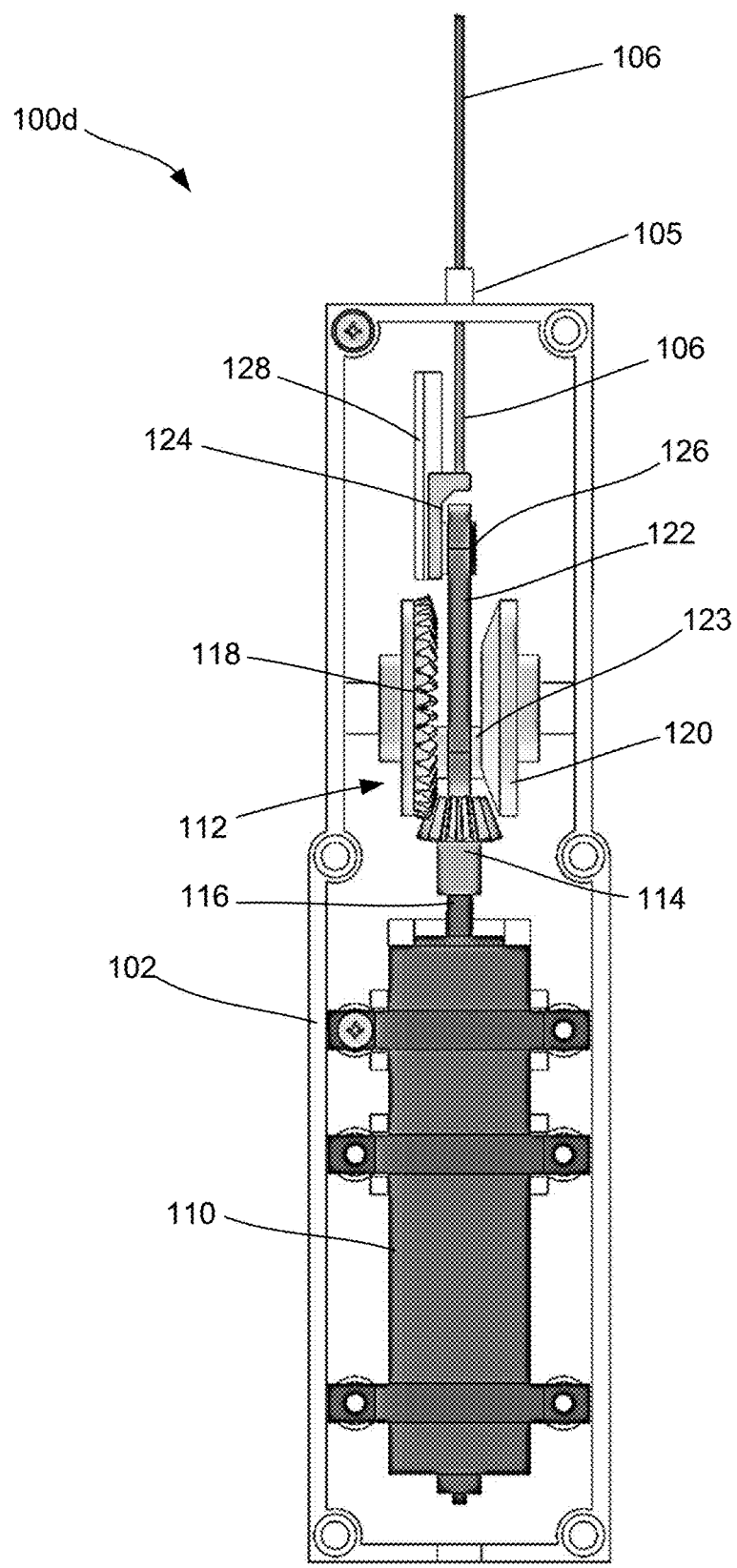
FIG. 9 is a side view, partly in section, of a fourth embodiment of a medical device of FIG. 2 consistent with the present disclosure.
Figure 10:
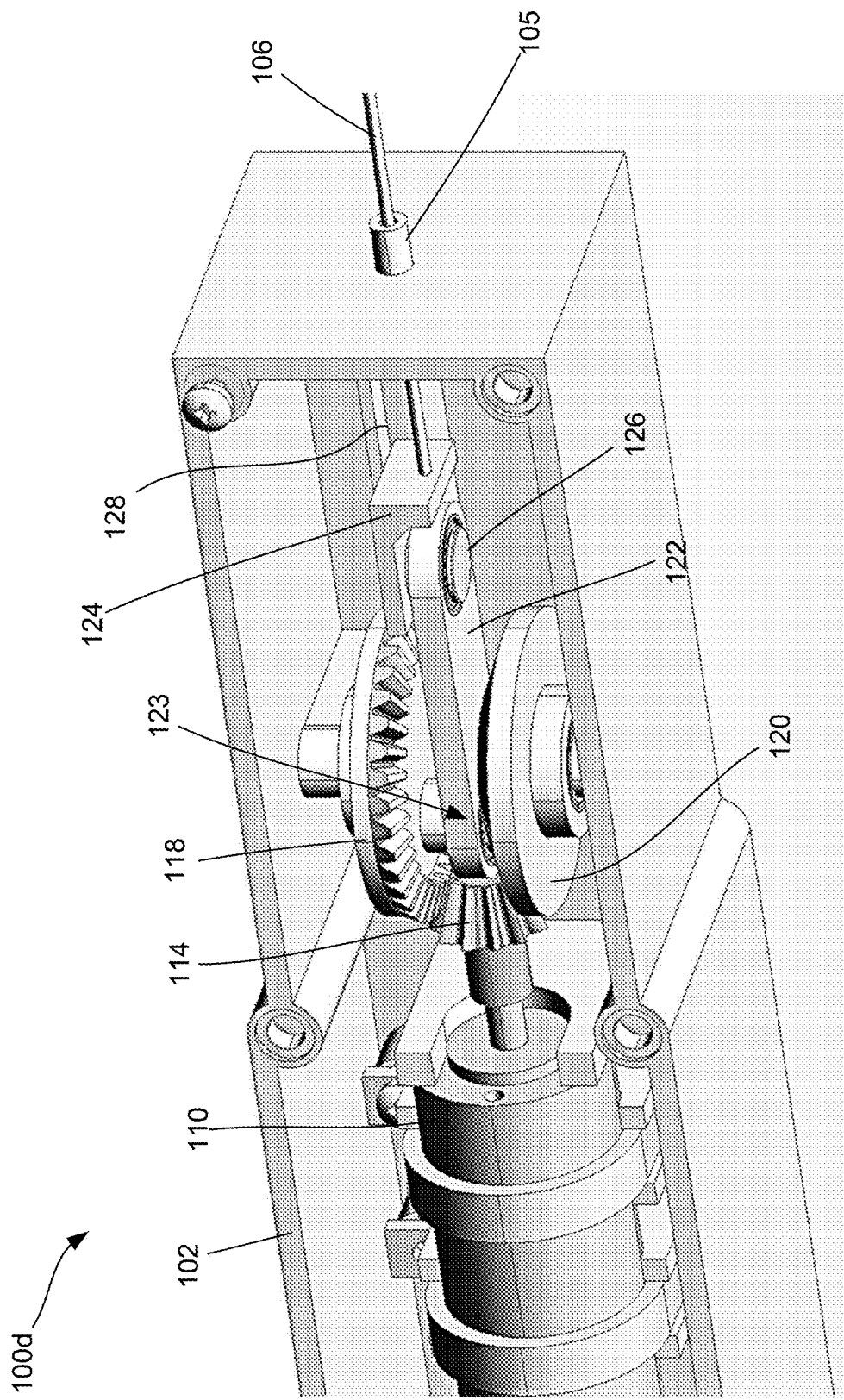
FIG. 10 is a perspective view, partly in section, of the medical device of FIG. 9.

FIG. 9 is a side view, partly in section, of a fourth embodiment of a medical device 100d consistent with the present disclosure. FIG. 10 is a perspective view, partly in section, of the medical device 100d illustrating further detail. As previously described, the device 100d includes an actuator member 110 disposed within the body 102 and coupled to the working instrument 106 via a gear assembly 112. In some embodiments, the actuator is a motor including a drive shaft 116 configured to rotate upon activation of the actuator (i.e., in response to user input). The gear assembly 112 may generally include a set of corresponding bevel gears, a first bevel gear 114 directly coupled to the actuator drive shaft 116 and having an axis aligned with an axis of the drive shaft 116 and thereby correspondingly rotate with the drive shaft 116 about a common axis, and a second bevel gear 118 positioned relative to the first bevel gear 114 such that the second bevel gear axis is approximately orthogonal to the first bevel gear axis (i.e., axes of the first and second bevel gear shafts intersect) and tooth-bearing faces of the first and second bevel gears correspondingly engage one another. The gear assembly 112 may act as a slider-crank mechanism to convert rotary motion (i.e., rotation of the first bevel gear 114 in response to operation of the actuator 110) to linear motion via rotation of the second bevel gear 118. In particular, a connecting rod 122 may be coupled at one end to a portion of the second bevel gear, as indicated at arrow 123 in FIG. 10, generally at a portion of the second bevel gear 118 a certain radius from the second bevel gear axis.

Figure 11:
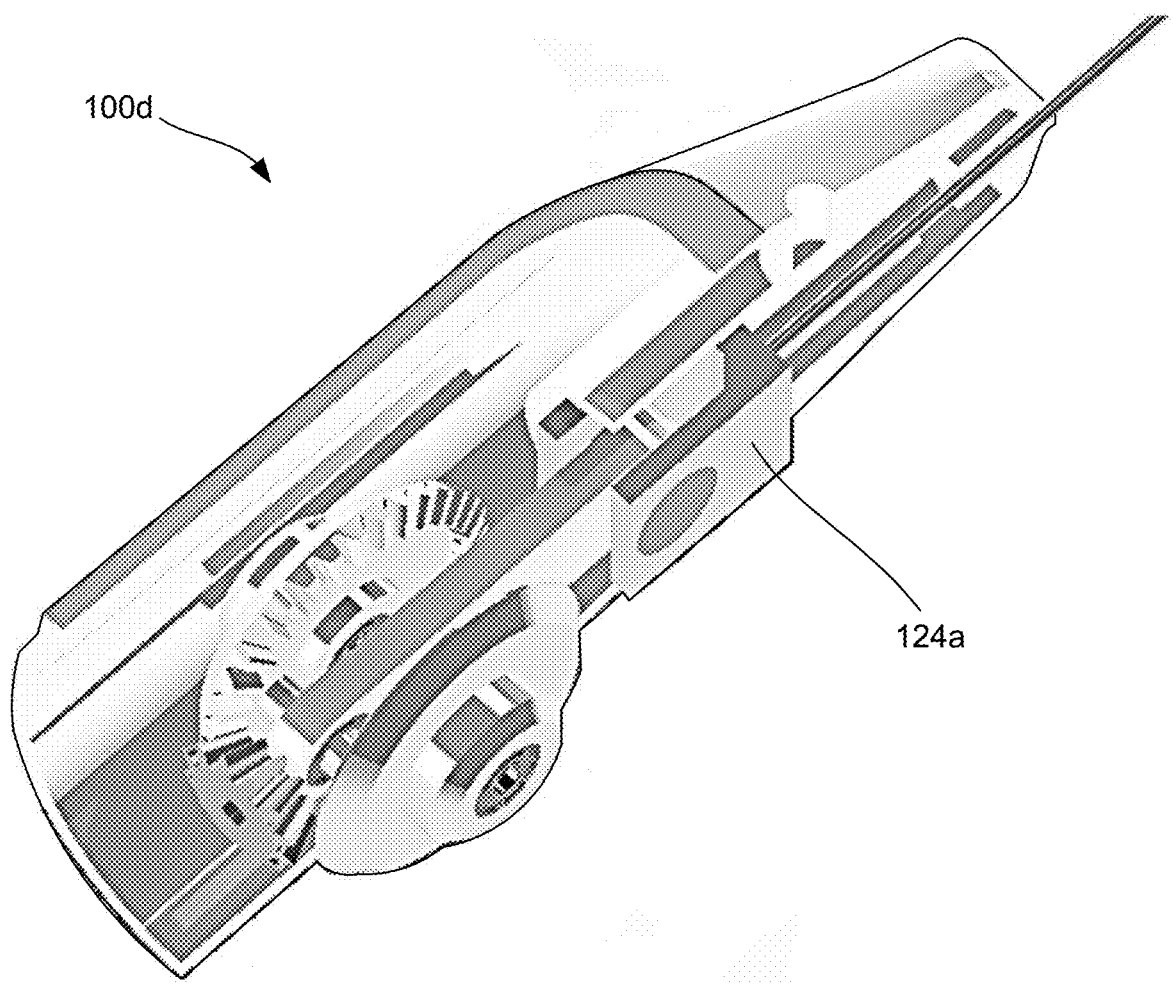
FIG. 11 is a perspective view, partly in section, of the medical device of FIG. 9 illustrating another embodiment of the linear oscillating member.

As shown, the gear assembly 112 may also include a corresponding wheel/disc portion opposing the second bevel gear 118 and coupling to one another at the point at which the connecting rod 122 is coupled thereto (see arrow 123). The connecting rod 122 is coupled at the other end to a linear oscillating member 124, via a pin 126 or the like, and the linear oscillating member 124 is affixed to, and in sliding engagement with, a track portion 128 of the body 102. FIG. 11 is a perspective view, partly in section, of the medical device 100d illustrating another embodiment of the linear oscillating member 124a. As shown, the linear oscillating member 124a has a knuckle type connection with the connecting rod.

Accordingly, rotation of the second bevel gear 118, in response to rotation of the first bevel gear 114, results in movement of the connecting rod 122, which creates linear oscillation of the linear oscillating member 124 (front and back motion along a longitudinal axis X of the body 102 of the device 100d), wherein the linear oscillating member 128 is configured to slide between an extended position (i.e., movement towards distal end of body) and a retracted position (i.e., movement towards proximal end of body), as generally directed by the track portion 128 containing the linear oscillating member 124. A proximal end of the working instrument 106 is coupled to the linear oscillating member 124, such that thee working instrument 106 linearly oscillates between retracted and extended positions in response to movement of the linear oscillating member 124. Accordingly, once the actuator member 110 is activated, it is configured to drive the gear assembly 112, which, in turn, slides the linear oscillating member 124 and in turn linearly oscillates the working instrument 106 generally along a longitudinal axis X of the body 102 between retracted and extended positions, such that, when in the extended position, the distal tip of the working instrument extends a distance past a distal end of the guide member and is able to engage target tissue and provide treatment.

Figure 12:
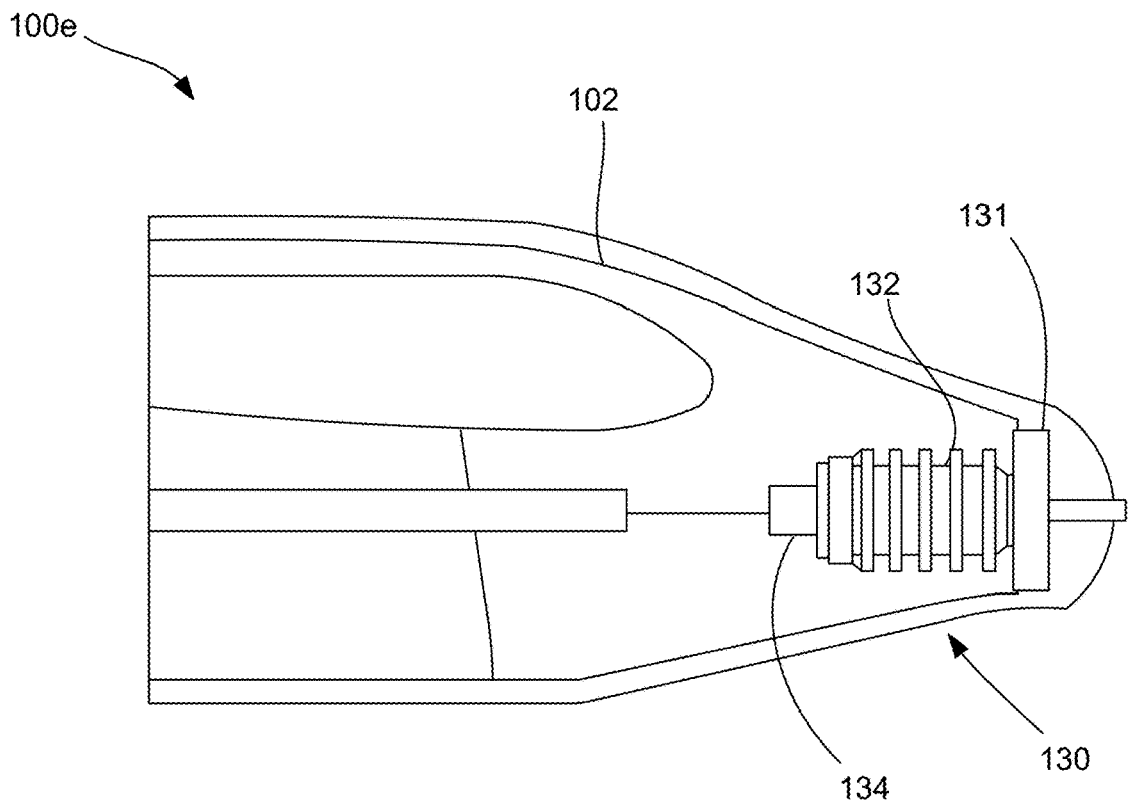
FIGS. 12 and 13 are side and perspective views, partly in section, of a medical device illustrating an attachment member for receiving a distal end of the working instrument and configured to be coupled to the linear oscillating member by way of a magnetic coupling interface.
Figure 13:
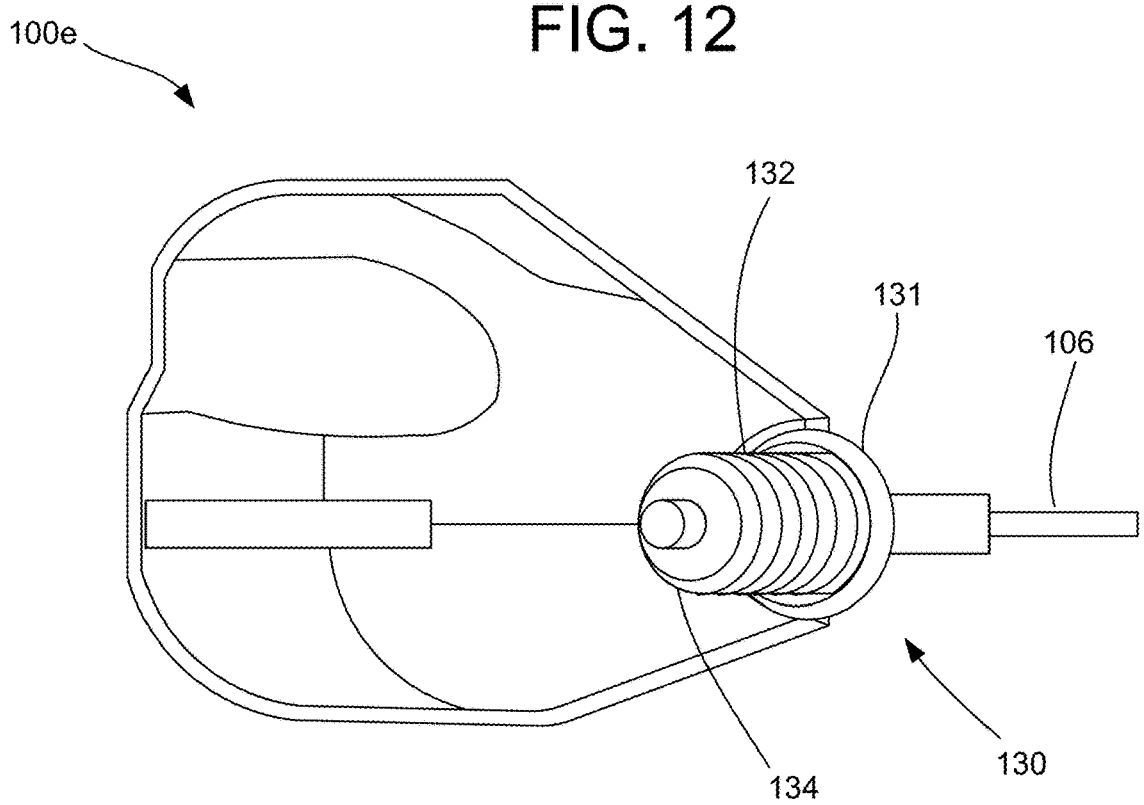

FIGS. 12 and 13 are side and perspective views, partly in section, of a medical device 100e, illustrating an attachment member 130 for removably attaching at least the working instrument 106 to the body 102 of the medical device 100 and into engagement with the actuator 110 and gear assembly 112. For example, the attachment member 130 may be provided within the body 102 of the device 100 and configured to receive and releasably retain at least a distal end of the working instrument 106 within and operably coupled to the actuator 110 and gear assembly 112. The attachment member 130 includes a flexible housing 132, which may include flexible walls configured to expand in a longitudinal direction along a length of the housing 132 from a distal end 131 to a proximal end 134. Accordingly, as shown, the housing 132 may resemble a bellow-type shape. The distal end 131 of the housing may include a flange member configured to engage and create a seal around an opening defined at the distal end of the body 102 of the device 100. The closed proximal end 134 of the housing 132 is either magnetized, composed of a magnetic material, or includes a magnetic material on an exterior portion thereof. Accordingly, the distal end 131 attachment member 130 may generally be fixed into engagement within the interior of the housing 102 of the device and the interior of the housing 132 may generally be aligned with an opening on the distal end of the body 102 of the device, such that, upon an operator inserting a working instrument 106 into the opening, the distal end of the working instrument 106 will continue to pass into the housing 132 and will eventually come into engagement with the proximal end 134 and be releasably retained therein. The interior of the attachment member 130 is essentially isolated from the remainder of the interior of the body 102 of the device 100, thereby maintaining the sterile field within the remainder of the body 102. Thus, upon use of the working instrument 106, an operator need only pull the working instrument 106 with sufficient force to become disengaged from the proximal end 134 of the housing 132 and then simply insert a new working instrument, for example, without concern of contaminating the device itself and thus allows for the device to be reused.

Figure 14A:
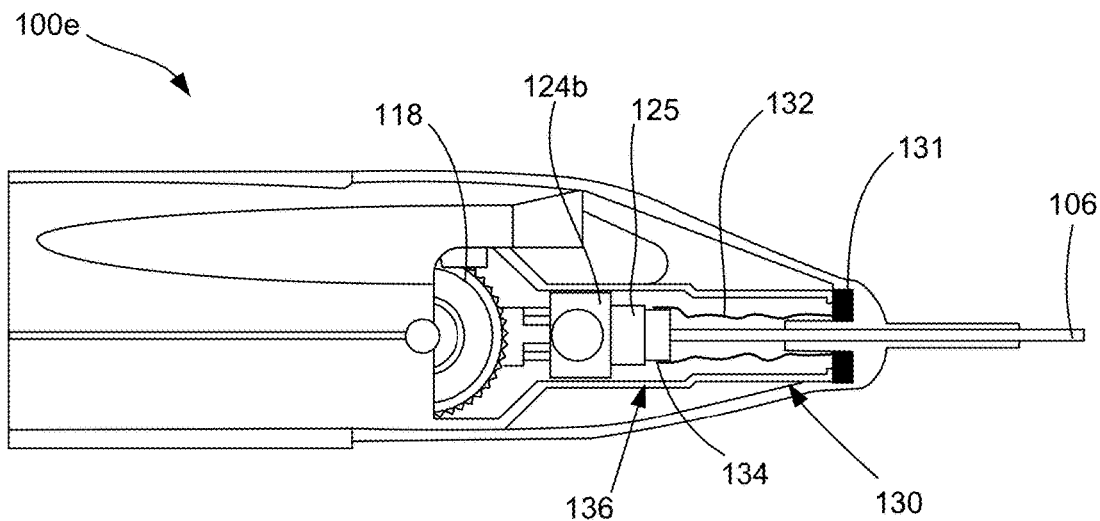
FIGS. 14A and 14B are side views, partly in section, of a medical device illustrating the working instrument linearly oscillating from a retracted position to an extended position in response to operation of the motor, which is operably coupled to the working instrument via the magnetic coupling interface.
Figure 14B:
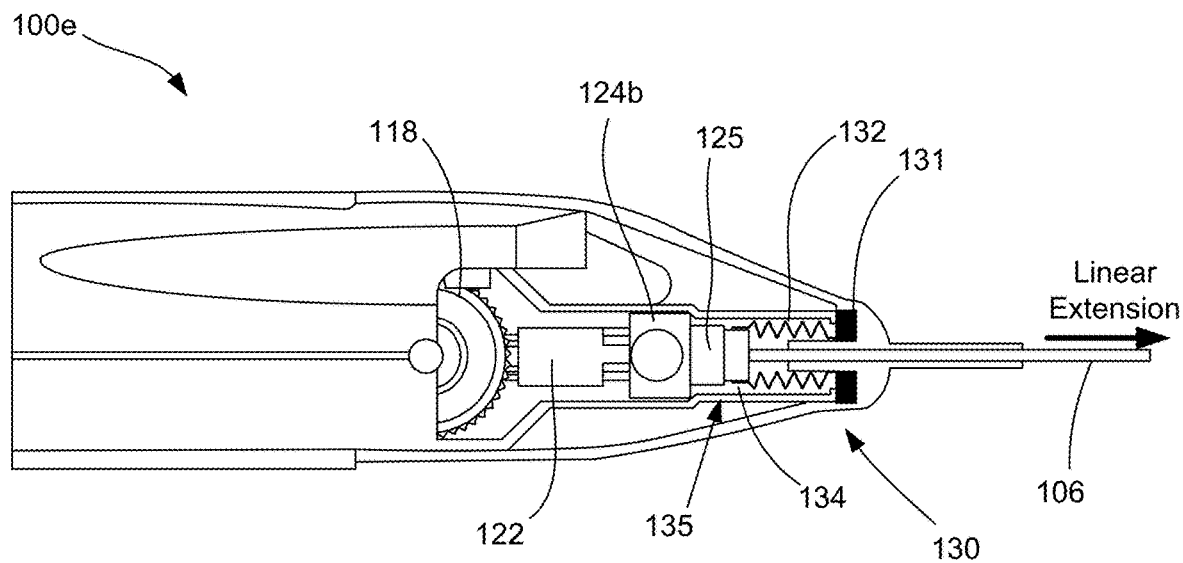

FIGS. 14A and 14B are side views, partly in section, of the medical device 100e illustrating the working instrument 106 linearly oscillating from a retracted position (FIG. 14A) to an extended position (FIG. 14B) in response to operation of the actuator 110, which is operably coupled to the working instrument 106 via a magnetic coupling interface. In particular, the linear oscillating member 124b may include a magnetic portion 125 configured to be magnetically coupled to the proximal end 134 of the housing 132 of the attachment member 130 by way of an attractive magnetic force. In some embodiments, the proximal end 134 may resemble and serve as a male portion of the magnetic coupling interface (i.e., a protrusion) while the magnetic portion 125 of the linear oscillating member 124b may resemble and serve as a female portion of the magnetic coupling interface (i.e., a recess for receiving the protrusion). Accordingly, upon activation of the actuator, the rotary to linear movement created by the gear assembly 112 results in oscillation of the linear oscillating member 124b, which in turn results in linear oscillation of the attachment member 130 magnetically coupled thereto, and ultimately the working instrument 106. Furthermore, the particular arrangement of the attachment member within the body 102 of the device 100 essentially creates a sterile field, specifically within the body 102. For example, the interior of the attachment member 130 is essentially isolated from the remainder of the interior of the body 102 of the device 100, thereby maintaining the sterile field within the remainder of the body 102. Furthermore, the magnetic coupling interface is positioned on a single side of the sterile field (i.e., provided within the interior of the second portion of the device), and thus does not cross over any sterile field when the two components are to be coupled to one another.

For example, once a procedure is complete, an operator need only disengage the working instrument 106 from the attachment member 130 by simply pulling the working instrument 106 out of engagement with the attachment member 130, wherein the used working instrument 106 can either be discarded or set aside for sterilization, and a new or sterile working instrument can be coupled to the attachment member. Thus, the tissue penetrating device allows for a relatively simple process of changing out tissue penetrating elements without the risk of breaching a sterile field of the device, thereby allowing for the device to be reused for multiple procedures with little to no risk of contamination. The configuration of the attachment member, specifically the sealed arrangement within the device, and the positioning of the magnetic coupling on a single side of the sterile field, allows for an operator to easily switch between the reusable portion (i.e., the device itself) and the disposable portion (i.e., the interchangeable tissue penetrating elements). Rather than risking breaching the field when coupling a disposable element to the reusable device, the operator need only bringing the components proximate each other, which is enough to initiate the magnetic coupling to form a completely ready-to-use device.

Furthermore, the simple coupling process of two components (i.e., the reusable device and the disposable working instruments) further allows for the tissue treatment system to include a kit, which may include a single body with multiple interchangeable instrument assemblies. For example, the kit may include a plurality of different kinds and/or sizes of working instruments and/or corresponding guide members.

As used in any embodiment herein, the term "module" may refer to software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. The modules may, collectively or individually, be embodied as circuitry that forms part of a larger system, for example, an integrated circuit (IC), system on-chip (SoC), desktop computers, laptop computers, tablet computers, servers, smart phones, etc.

Any of the operations described herein may be implemented in a system that includes one or more storage mediums having stored thereon, individually or in combination, instructions that when executed by one or more processors perform the methods. Here, the processor may include, for example, a server CPU, a mobile device CPU, and/or other programmable circuitry.

Also, it is intended that operations described herein may be distributed across a plurality of physical devices, such as processing structures at more than one different physical location. The storage medium may include any type of tangible medium, for example, any type of disk including hard disks, floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, Solid State Disks (SSDs), magnetic or optical cards, or any type of media suitable for storing electronic instructions. Other embodiments may be implemented as software modules executed by a programmable control device. The storage medium may be non-transitory.

As described herein, various embodiments may be implemented using hardware elements, software elements, or any combination thereof. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A tissue penetrating device, the device comprising:
a first portion housing a motor; and
a second portion housing at least a distal portion of a tissue penetrating element, wherein the tissue penetrating element is operably coupled to the motor via a magnetic coupling, which coupling resides on a single side of a sterile field,
wherein the magnetic coupling comprises an attachment member housed within the second portion; and
wherein the attachment member comprises a housing including a closed proximal end and an open distal end and a length defined therebetween, wherein an edge of the open distal end is sealed into engagement with an interior of the second portion, thereby isolating an interior of the housing from a remainder of the first and second portions of the tissue penetrating device, and thereby creating the sterile field external of the attachment member.

2. The device of claim 1, wherein the open distal end is aligned with an opening at a distal end of the second portion such that distal portion of the tissue penetrating element extends therethrough and into the interior of the housing of the attachment member, wherein the distal end of the tissue penetrating element engages and is releasably retained within the closed proximal end of the attachment member.

3. The device of claim 2, wherein the proximal end of the attachment member comprises a magnetic coupling member coupled to a corresponding magnetic coupling member provided on a linear oscillating member operably coupled to the motor.

4. The device of claim 3, wherein, when the linear oscillating member is oscillated by the motor, the linear oscillating member further oscillates the proximal end of the attachment member and thereby oscillates the tissue penetrating element.

5. The device of claim 4, further comprising a gear assembly operably coupled to the motor and the tissue penetrating element, wherein the gear assembly is configured to convert rotary motion of the motor to linear motion to oscillate the tissue penetrating element.

6. The device of claim 5, wherein the gear assembly comprises: a first bevel gear directly coupled to a drive shaft of the motor and having an axis aligned with an axis of the drive shaft to thereby correspondingly rotate with the drive shaft about a common axis; and a second bevel gear positioned relative to the first bevel gear such that the second bevel gear axis is approximately orthogonal to the first bevel gear axis and tooth-bearing faces of the first and second bevel gears correspondingly engage one another.

7. The device of claim 6, further comprising a connecting rod having a first end directly coupled to a portion of the second bevel gear and a second end directly coupled the linear oscillating member, wherein the connecting rod oscillates in response to rotation of the first bevel gear, thereby resulting in oscillation of the linear oscillating member.

8. The device of claim 1, wherein the housing of the attachment member comprises a flexible wall configured to expand and compress in a longitudinal direction along a length of the housing from a distal end to a proximal end to accommodate oscillation.

* * * * *